United States Patent [19]

Manska

[11] Patent Number: 4,919,167

[45] Date of Patent: Apr. 24, 1990

[54] CHECK VALVE

[76] Inventor: Wayne E. Manska, 1921 Kellogg Dr., Anaheim, Calif. 92807

[21] Appl. No.: 325,551

[22] Filed: Mar. 17, 1989

[51] Int. Cl.⁵ .............................................. F16K 15/14
[52] U.S. Cl. ............................... 137/512; 29/890.124; 137/853; 137/854; 604/247
[58] Field of Search .................... 29/157.1 R; 137/843, 137/852, 853, 854, 512; 604/247

[56]  References Cited

U.S. PATENT DOCUMENTS

| 1,746,855 | 2/1930 | French . |
| 2,743,724 | 5/1956 | Gispen . |
| 3,010,477 | 11/1961 | Graham . |
| 3,383,113 | 5/1968 | McCandless . |
| 3,583,430 | 6/1971 | Toennesen . |
| 3,601,151 | 8/1971 | Winnard . |
| 3,601,152 | 8/1971 | Kenworthy ......................... 137/843 |
| 3,692,071 | 9/1972 | Begleiter . |
| 4,063,555 | 12/1977 | Ulinder ........................... 137/853 X |
| 4,194,435 | 3/1980 | Gaun . |
| 4,214,607 | 7/1980 | Beouteille . |
| 4,346,704 | 8/1982 | Kulle . |
| 4,535,818 | 8/1985 | Duncan et al. . |
| 4,535,819 | 8/1985 | Atkinson et al. . |
| 4,566,493 | 1/1986 | Edwards . |
| 4,568,333 | 2/1986 | Sawyer . |
| 4,780,378 | 10/1988 | McCartney ..................... 137/853 X |

FOREIGN PATENT DOCUMENTS 3319625  6/1984  Fed. Rep. of Germany .

OTHER PUBLICATIONS

Advertisement by Vernay Labs, 1987.
Advertisement by Burron Medical, 1987.

Primary Examiner—Robert G. Nilson
Attorney, Agent, or Firm—Knobbe, Martens, Olson & Bear

[57]  ABSTRACT

A check valve for providing mono-directional flow in medical devices. The check valve includes a valving means comprised of a valve member and a seat member disposed within a cylindrical channel. The valve member is coaxially aligned within the channel downstream of the seat member and provides a valve cavity into which a portion of the seat member is disposed. The interface between the valve member and the seat member creates a seal length. The valve member is radially stressed by the axial position of the seat member so that the sealing force along the seal length is substantially radial. Fluid flow passes through an axial bore in the valve seat member and upon sufficient pressure unseats the seal length and passes through the annular passageway between the valve member and the seat member.

26 Claims, 1 Drawing Sheet

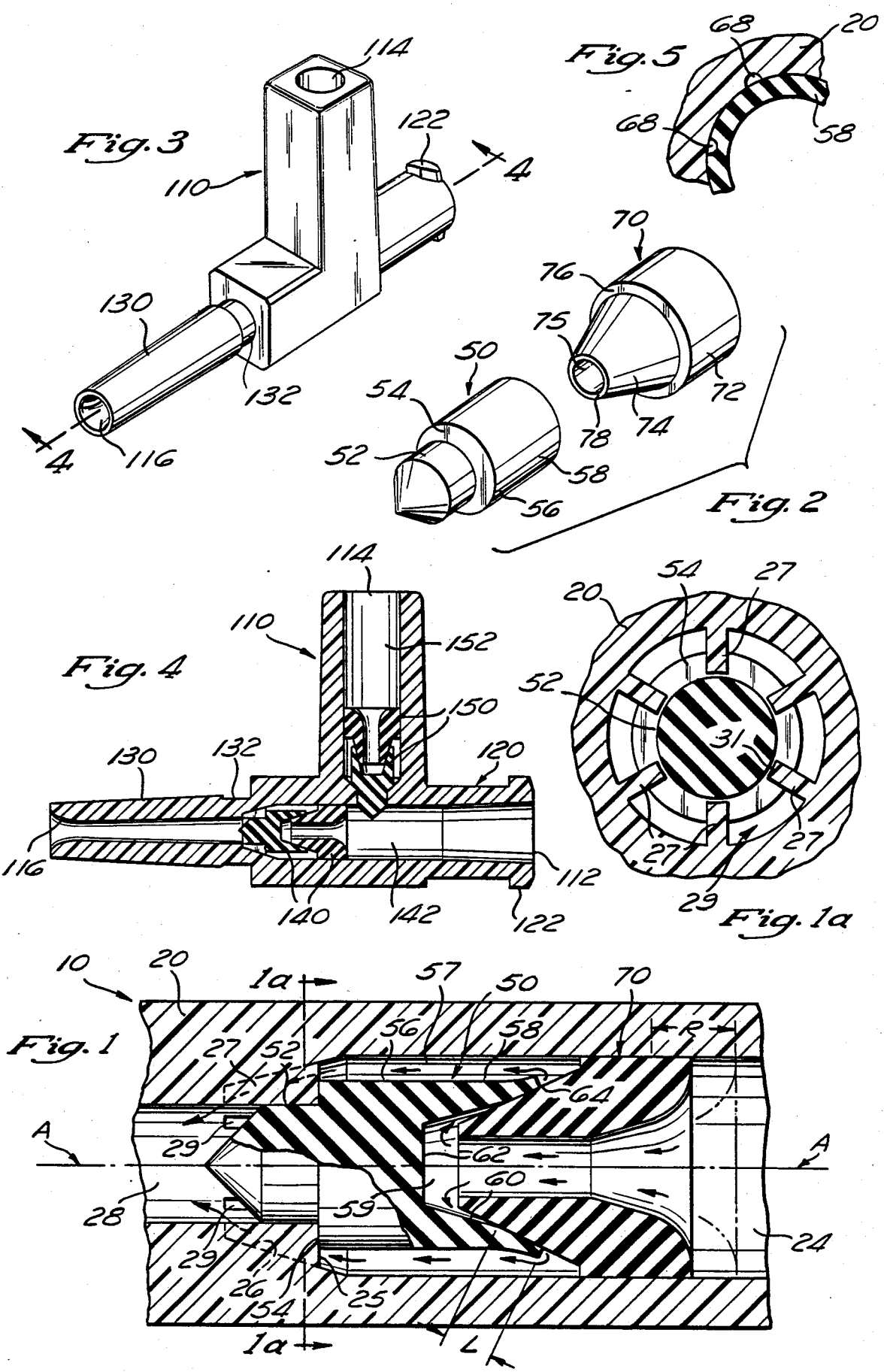

CHECK VALVE

BACKGROUND OF THE INVENTION

This invention relates to mono-directional flow valving for medical and laboratory apparatus. In particular, the present invention concerns a medical check valve which has a predetermined cracking pressure while ensuring fluid flow through the valve in only one direction.

Check valves are widely used in medical systems to prevent reverse fluid flow, e.g., in catheters and intravenous lines. U.S. Pat. No. 3,601,151 to Winnard shows a check valve assembly employing an elastomeric sock member which surrounds the end of the cylindrical stem. The cylindrical stem passes fluid through a centrally disposed axial bore. In its neutral configuration, the elasticity of the sock member seats the sock on the cylindrical surface of the stem thereby preventing fluid flow through the stem. Upon sufficient fluid pressure within the stem bore, the elastic sock expands to permit the passage of the fluid between the sock and the outside of the stem. Reverse pressure forces the sock against the cylindrical surface and this prevents flow in the reverse direction. However, if the reverse pressure is high, the sock member may be subject to rupture. Because the sock and stem must be specially sized for each particular cracking pressure, this type of valve is expensive to manufacture where valves of different cracking pressures are desired. Also, the size variation of the components due to manufacturing tolerances prohibits the production of valves from standard components having a common cracking pressure.

SUMMARY OF THE INVENTION

The check valve of the present invention comprises components which can be assembled to yield a check valve having any cracking pressure within a predetermined range of cracking pressures.

The present invention employs a valving assembly disposed in a tubular channel within a housing. The housing may be connected to a medical line to provide mono-directional valving in the line. In the preferred embodiment, the housing includes a tubular channel having an inlet section and an outlet section of different diameters, wherein the inlet section has a larger diameter than the outlet section. Preferably, a transition section joins the inlet section to the outlet section and is defined by a plurality of radial ribs within the channel. The ribs create lumens through which the fluid stream may pass.

The valving assembly is comprised of a seat member and a valve member disposed within the housing. Preferably, the seat member and the valve member are disposed within the channel such that the seat member is upstream of the valve member.

In the preferred embodiment, the seat member includes a retaining portion and a seating portion. A concentric axial passageway through the seat member provides a flow path through the seat member. The retaining portion is sized to provide a friction fit with the wall of the inlet section, thereby securing the seat member with respect to the housing. Alternatively or additionally, the seat member may be bonded or ultrasonically welded to the inlet section wall. Preferably, the seating portion of the seat member has a frusto-conical configuration which is sized to engage the valve member.

The valve member is comprised of a body portion which is sealingly connected to an elastomeric valve flange portion on the upstream end of the body portion. In the preferred embodiment, the inner surface of the valve flange portion defines a frusto-conical valve cavity sized to engage the seating portion of the seat member. In the preferred embodiment, the downstream end of the valve member includes an orientation portion coaxially aligned with the body portion. Preferably, the orientation portion is sized to be slidably received within a passageway defined by the radial ribs of the transition section.

In the assembled configuration of the preferred embodiment, the frusto-conical seating portion of the seat member is partially disposed within the frusto-conical valve cavity so that the inner surface of the valve flange portion sealingly contacts the seating portion, thereby providing a circumferential seal having an axial seal length. Either the seat member or the valve member or both the seat member and the valve member may be of a frusto-conical configuration. Such sealing contact yields a sealing force between the seating portion and the valve flange portion along the seal length. This sealing force is comprised of an axial component and a radial component, wherein the radial component is substantially greater than the axial component. The sealing force provides a specific cracking pressure for the valve.

The sealing force between the inner surface of the valve flange portion and the seating portion is a function of the axial displacement of the valve member relative to the seat member. The sensitivity of sealing force to the relative axial position of the seat member and valve member is determined by the configuration of the seat member and the valve member, such as the relative conical angles of these members. In the preferred embodiment, the inner surface of the valve flange portion subtends a smaller conical angle than the seating portion.

The valve flange portion of the preferred embodiment is elastomeric while the sealing portion is rigid. In the presence of flow in the forward direction at a pressure which is equal to the cracking pressure (i.e., the minimal upstream pressure at which the check valve will permit mono-directional flow), the valve flange portion expands to form an annular passage between the seating portion and the valve flange portion. The expansion is well within the elastic limit of the elastomer so that when the upstream pressure is reduced below the cracking pressure, the elastic memory of the elastomer returns the flange to the original sealed position.

In addition, the seal length between the valve member and the seat member is sufficiently long to inhibit the passage of fluid between the valve member and the seat member in the event that small particulate matter carried by the flow becomes trapped between the seat member and the valve member.

Upon actuation of the disclosed check valve, the flow path through the valve is radially symmetrical. The symmetry of the flow stream washes air bubbles from the check valve, so that the medical line can be freed of trapped air.

DETAILED DESCRIPTION OF THE DRAWINGS

FIG. 1 is a partial cross-sectional view of the present invention showing the valve member and the seat member disposed within a channel;

FIG. 1a is a cross-sectional view taken along line 1a—1a of FIG. 1 showing the valve member disposed within the housing;

FIG. 2 is a perspective of the valve member and the seat member showing the passageway in the seat member;

FIG. 3 is a perspective of the present invention employed in a dual check valve showing standard male and female luer fittings;

FIG. 4 is a cross-sectional view taken along line 4—4 of FIG. 3 showing the orientation of the individual check valves within the dual check valve; and FIG. 5 is a partial cross-sectional view of an expanded valve flange portion showing the capillary passageways between the housing and the valve flange portion.

DETAILED DESCRIPTION OF THE PREFERRED EMBODIMENT

Referring to FIG. 1, the check valve 10 of the present invention includes a seat member 70 and a valve member 50 disposed within a housing 20.

As shown in FIG. 1, the housing 20 includes a tubular channel having a central axis A. The tubular channel comprises a tubular inlet section 24 having a uniform cylindrical length coaxially aligned with the axis A and connected to a transition section 26, also coaxially aligned with the axis A. The transition section 26 is connected to an outlet section 28 which is coaxially aligned with the axis A. The inlet section 24, the transition section 26 and the outlet section 28 are defined by circular cross-sections, wherein the diameter of the inlet section 24 is larger than the diameter of the outlet section 28. The transition section 26 provides a step between the inlet section 24 and the outlet section 28. By way of example, the housing 20 may be constructed of a rigid plastic material which is inert with respect to the fluid transported through the check valve 10.

As shown in FIG. 1, the transition section 26 includes a plurality of axially oriented ribs 27 which extend radially inward around the periphery of the transition section 26. Referring to FIG. 1a, the inward edges 31 of the ribs 27 define a channel diameter substantially equal to that of the outlet section 28. The upstream end of the ribs 27 creates a stop 25. The stop 25 is sized to have a sufficient radial dimension so as to engage a shoulder 54 of the valve member 50. The areas between the ribs 27 create lumens 29 for the passage of fluid through the transition section 26, as shown by the arrows in FIG. 1.

Referring to FIG. 2, the seat member 70 includes a cylindrical retaining portion 72 coaxially aligned with an integral frusto-conical seating portion 74. The diameter of the retaining portion 72 is sized to create an interference fit with the cylindrical interior wall of the inlet section 24. The frusto-conical configuration of the seating portion 74 is axially defined by a secured annular end 76 at the junction of the retaining portion 72 and the seating portion 74, and by a free annular end 78 of the seating portion 74. The secured annular end 76 has a circumference greater than the circumference of the free annular end 78. The seat member 70 includes a coaxial passageway 75 through the retaining portion 72 and the seating portion 74. The passageway 75 permits fluid flow through the seat member 70.

Referring to FIGS. 1 and 2, the valve member 50 includes a solid cylindrical body portion 56, a valve flange portion 58 on one end of the cylindrical body portion 56, and an orientation portion 52 on the other end of the cylindrical body portion 56. The body portion 56, the valve flange portion 58 and the orientation portion 52 can be integrally formed and coaxially aligned with the seat member 70. The valve member 50 may be constructed from a material which is inert with respect to the fluid passed through the check valve 10. Referring to FIG. 1, the valve flange portion 58 is joined to the upstream end of the body portion 56. The body portion 56 has a diameter significantly less than the diameter of the cylindrical inlet section 24 so as to provide a uniform annular flow path 57 between the wall of the inlet section 24 and the body portion 56. The annular flow path 57 is a radially symmetrical area through which the flow passes. Therefore, the flow is radially symmetric as it passes through the annular flow path 57. Because of the radial symmetry of the flow through the annular flow path 57, there is no preferred flow stream through the annular flow path 57. Therefore, the flow through the annular flow path 57 does not create voids or air bubbles within the flow stream. Further, the radially symmetric flow through the check valve 10 washes air bubbles from the check valve 10 so that the flow stream through the check valve 10 is free of air bubbles.

As shown in FIG. 1, the valve flange portion 58 includes a frusto-conical valve cavity 59 which receives the seating portion 74 of the seat member 70. The frusto-conical valve cavity 59 is defined by an inner surface 60 of the valve flange portion 58 and the body portion 56. The inner surface 60 of the cavity 59 is defined by a secured cavity end 62 and a free cavity end 64. The frusto-conical valve cavity 59 is configured such that the circumference of the secured cavity end 62 is smaller than the circumference of the free cavity end 64. The secured end 62 of the frusto-conical valve cavity 59, is closed and sealed by the upstream end of the body portion 56. In the assembled configuration, the frusto-conical valve cavity 59 is exposed to the upstream pressure as the flow passes through the axial passageway 75 of the seat member 70.

Referring to FIGS. 1 and 2, the valve member 50 includes the orientation portion 52 disposed on the downstream end of the body portion 56. The orientation portion 56 is of a cylindrical configuration, having a diameter that is less than the diameter of the body portion 56 and sized to be slidably received within the channel defined by the inner edges 31 of the ribs 27. The transition between the diameter of the orientation portion 52 and the diameter of the body portion 56 creates an annular shoulder 54. The shoulder 54 is sized to engage the stop 25. Contact of the shoulder 54 with the stop 25 prevents axial displacement of the valve member 50 in the downstream direction. As shown by the arrows representing the flow path in FIG. 1, the lumens 29 between the ribs 27 allows fluid to pass through the transition section 26, around the orientation portion 52 as it is disposed within the channel defined by the inner edges 31 of the ribs 27, and into the outlet section 28. As shown in FIG. 1, the lumens 29 extend downstream beyond the contact area of the orientation portion 52 and the ribs 27. Therefore, the flow path through the lumens 29 to the outlet section 28 is unobstructed by the orientation portion 52.

Referring to FIG. 1, the frusto-conical valve cavity 59 is configured such that the circumference of the free cavity end 64 receives the free annular end 78 of the seating portion 74. The inner cavity surface 60 contacts the seating portion 74 to provide an interface between the seat member 70 and the valve member 50, creating a seal length L therebetween. As shown in FIG. 1, the seating portion 74 subtends a larger conical angle than the inner surface 60 of the valve flange portion 58. However, the seating portion 74 could be formed to subtend a smaller conical angle than the inner surface 60 of the valve flange portion 58. Also, the check valve 10 may be configured so that the seating portion 74 is cylindrical and the inner surface 60 of the valve flange portion 58 is frusto-conical. Alternatively, the seating portion 74 may be frusto-conical and the inner surface 60 of the valve flange portion 58 may be cylindrical. Also, both the seating portion 74 and the inner surface 60 of the valve flange portion 58 may be frusto-conical and subtend equivalent conical angles.

In assembling the check valve 10, the valve member 50 is inserted into the housing 20 so that the orientation portion 52 is received within the passage defined by the inner edges 31 of the ribs 27, and the shoulder 54 engages the stop 25. The positioning of the orientation portion 52 within the channel defined by the inner edges 31 of the ribs 27 ensures that the valve member 50 is coaxially disposed with respect to the inlet section 24. Referring to FIG. 1, the annular flow path 57 between the wall of the inlet section 24 and the valve member 50 is maintained by the coaxial alignment of the valve member 50 within the inlet section 24.

The seat member 70 is then disposed within the housing 20 through the inlet section 24, wherein the seating portion 74 is oriented towards the valve member 50. The diameter of the retaining portion 72 is sized to provide a friction fit between the wall of the inlet section 24 and the retaining portion 72. The friction forces should be substantially greater than any force to be generated by fluid pressures, either forward or reverse, within the check valve 10. The seat member 70 is disposed within the inlet section 24 so that the seating portion 74 contacts the inner surface 60 of the valve flange portion 58.

As the seating portion 74 engages the inner surface 60, downstream axial displacement of the valve member 50 is precluded by the engagement of the shoulder 54 against the stop 25. Therefore, the axial displacement of the seat member 70 toward the valve member 50 causes the inner surface 60 to engage the seating portion 74. As shown in FIG. 1, the taper of the seating portion 74 radially displaces the valve flange portion 58 from its unstressed configuration. The interface between the inner surface 60 and the seating portion 74 creates a circumferential seal having a seal length L determined by the axial displacement of the seat member 70 relative to the valve member 50.

When the insertion force is removed from the seat member 70, the friction fit between the retaining portion 72 and the wall of the inlet section 24 prevents subsequent movement of the seat member 70 relative to the housing 20. Subsequently, the seat member 70 can be further secured to the housing 20 by means of bonding agents or ultrasonic welding.

The cracking pressure of the check valve 10 is a function of the degree of radial stress of the valve flange portion 58, and this radial stress of the valve flange portion 58 is a function of the axial displacement of the seat member 70 with respect to the valve member 50. Therefore, a predetermined cracking pressure may be obtained through the selective axial placement of the seat member 70 relative to the valve member 50 when the valve is assembled. This feature is highly advantageous in that valves of various cracking pressures can be assembled from identical parts. By properly positioning the components of the valve, it is possible to obtain any desired cracking pressure within a predetermined range of cracking pressures. As shown in FIG. 1, the seat member 70 may be disposed at any axial position within an adjustment range R, to yield the desired cracking pressure.

The relationship between the axial displacement of the seat member 50 and the cracking pressure is also a function of the configuration of the seating portion 74 and the valve flange portion 58. Therefore, the sensitivity of the cracking pressure to axial displacement of the seating portion 74 may vary depending on the particular configurations of the seating portion 74 and the valve flange portion 58.

The seating portion 74 may be formed of a relatively rigid plastic material, while the valve flange portion 58 preferably comprises an elastomeric material which exhibits a force proportional to the degree of stress exerted on the material. The force between the seating portion 74 and the valve flange portion 58 is comprised of an axial component and a radial component, and the frusto-conical angles of the seating portion 74 and the valve flange portion 58 are relatively configured such that the radial component is substantially greater than the axial component. Either the seating portion 74 or the valve flange portion 58, or both the seating portion 74 and the valve flange portion 58 may be of a frusto-conical configuration wherein the radial component of the force between the seating portion 74 and the valve flange portion 58 is substantially greater than the axial component.

The valve flange portion 58 creates radial forces against the seating portion 74 over the seal length L and these forces define the cracking pressure for the check valve 10. When the upstream fluid pressure is sufficiently great to overcome the radial forces acting over the seal length L, the inner cavity surface 60 of the valve flange portion 58 separates from the seating portion 74 and fluid passes through the check valve 10. Therefore, upon a sufficient upstream fluid pressure, the inner cavity surface 60 is unseated from the seating portion 74 and fluid passes through the check valve 10. The frusto-conical configuration of the inner surface 60 and the seating portion 74 provide that upon a fluid pressure greater than the cracking pressure, the flow path between the seating portion 74 and the inner surface 60 is an annular passage. The elastomeric material of the valve flange portion 74 should be sufficiently elastic to permit the flange 74 to expand such that the annular passage thus created has a cross-sectional area which is approximately at least as great as the cross-sectional area of the narrowest portion of the passageway 75. Therefore, when the upstream fluid pressure is greater than the cracking pressure, the maximum flow rate through the check valve 10 is limited by the cross-sectional area of the passageway 75 rather than the annular passageway between the seating portion 74 and the inner surface 60. As shown by the arrows in FIG. 1, the fluid then passes through the annular flow path 57 between the valve member 50 and the wall of the inlet section 24, through the lumens 29, and exits through the outlet section 28.

In some applications, it may be preferable that the elastomeric material be sufficiently elastic to allow the valve flange portion 58 to expand to the wall of the inlet section 24 when a very high upstream pressure surge occurs. As shown in the partial cross-sectional view of FIG. 5, the high pressure surge thereby presses the valve flange portion 58 against the interior wall of the inlet section 24 until the pressure is reduced. The contact of the valve flange portion 58 and the interior wall of the inlet section 24 prevents high pressure surges from passing downstream through the check valve 10.

The check valve 10 may include a relief passage 68 to permit a limited flow rate through the check valve 10 when the valve flange portion 58 has been expanded to contact the wall of the inlet section 24 during high pressure surges. As shown in FIG. 5, the housing 20 may include the relief passage 68. The relief passage 68 has an axial dimension greater than the length of contact between the valve flange portion 58 and the interior wall of the inlet section 24 during high pressure conditions. The relief passage 68 permits a limited fluid flow through the check valve 10 during high pressure surges. Alternatively, or additionally, the outside of the valve flange portion 58 may include a relief passage 68. The cross-sectional area of the relief passage 68 is determined by the desired flow rate through the check valve 10 during high pressure conditions or surges. If a large flow rate through the check valve 10 during high pressure surges is desired, the cross-sectional area and number of relief passages 68 may be increased to allow for the desired flow rate.

Alternatively, the relief passage 68 may be of a sufficiently small cross-sectional area so that any flow through the relief passage 68 is substantially independent of the upstream pressure. Downstream, such a flow has a substantially lower pressure than the high upstream pressure which causes the valve flange portion 58 to contact the interior wall of the inlet section 24. Therefore, the pressure of the fluid flow downstream of the relief passage 68 is reduced so that downstream equipment is not damaged by the upstream pressure surge.

Upon a reverse pressure (i.e., a downstream pressure which is greater than the upstream pressure) within the check valve 10, the outside surface of the valve flange portion 58 is exposed to a higher pressure than the inner cavity surface 60. The pressure gradient across the valve flange portion 58 results in a net inward radial force acting on the valve flange portion 58. The net inward radial force is directed toward the seating portion 74 so that the valve flange portion 58 is biased against the seating portion 74. The reverse pressure also exerts an axial force on the valve member 50, which may drive the valve member 50 towards the seat member 70. The seating portion 74 is thereby further received within the valve flange portion 58. The reverse pressure thus tends to further displace the inner surface 60 onto the seating portion 74, thereby increasing the seal length L. The axial displacement of the valve member 50 toward the seat member 70 causes the shoulder 54 to disengage the stop 25. The orientation portion 52 has an axial dimension so that a sufficient length of the orientation portion 52 remains within the passage defined by the ribs 27, to ensure that the valve member 50 remains in a coaxial configuration with respect to the axis A and the seat member 70. Upon a renewed upstream flow pressure, the elastomeric bias of the valve flange portion 58, may combine with the upstream flow pressure to displace the valve member 50 to its original configuration wherein the shoulder 54 abuts the stop 25 and the seal length L returns to its original length with the cracking pressure at its original value.

As shown in FIGS. 3 and 4, the present invention may be employed in a dual check valve 110. The dual check valve 110 preferably incorporates a male 130 and female luer fitting 120 which are concentric with respect to each other. The female luer 120 has a 0.170 inch diameter opening at the inlet port 112 and a reducing conical taper of 0.060 inch/inch. The male luer 130 has an end diameter of 0.155 inches at the outlet port 116 and an expanding conical taper of 0.060 inch/inch. The resulting nominal engagement of female and male luer fittings 120,130 is 0.250 inch. To assure a sufficient seal between female and male luer fittings 120,130, it is desirable to have male-female interface contact for the full length of their engagement. Therefore, the female luer taper typically extends for a minimum length of 0.250 inches at which point the female luer exhibits a diameter of 0.155 inches. Beyond the 0.250 inch depth, the channel may deviate from the female luer conical angle or become cylindrical. The preferred cylindrical diameter is accordingly less than or equal to the diameter of the reduced end of the female luer taper. A valve member and a seat member may then be disposed within a housing which has a standard female luer fitting 120 such as is depicted in FIGS. 3 and 4. This configuration permits the simple, advantageous and cost effective installation of valve member 50 and the seat member 70 through the female luer 120.

Therefore, any housing having a standard female luer fitting 130 and an appropriately configured channel may have a valve member and a seat member loaded into the housing to exhibit any cracking pressure within the predetermined range.

Referring to FIGS. 3 and 4, the female luer fitting 120 includes threads 122 disposed at the proximal end of the female luer fitting 120. The threads 122 engage a luer nut (not shown) in the standard connection with a standard male luer fitting of a device (not shown).

The dual check valve 110 may also incorporate a secondary inlet port 114 which provides a second inlet to the dual check valve 110 and may include either a male or female luer fitting or a bondable sleeve-type fitting for tubing.

As shown in FIG. 4, the dual check valve 110 is comprised of two check valves. A primary check valve 140 is disposed within a primary tubular channel 142 which connects the inlet port 112 and the outlet port 116.

A secondary channel 152 perpendicularly intersects the primary channel 142 between the primary check valve 140 and the inlet port 112. A secondary check valve 150 is disposed within the secondary channel 152. As shown in FIG. 4, the secondary check valve 150 is disposed proximal to the intersection of the secondary channel 152 and the primary channel 142. The distance between the primary channel 142 and the secondary check valve 150 is minimized to reduce the formation of air pockets at the downstream end of the secondary check valve 150 and to increase the removal of air bubbles upon a flow through the secondary check valve 150.

The dual check valve 110 permits the selective transfer of fluid from a secondary receptacle (not shown) sealably connected to the secondary port to a primary receptacle (not shown) sealably connected to the outlet port 116. Fluid may be drawn from the secondary receptacle through the secondary check valve 150 by the creation of a sufficient negative pressure at the inlet port 112 or by a sufficient positive pressure at the secondary inlet port 114. The negative pressure at the inlet port 112 may be created by use of a syringe (not shown) attached to the inlet port 112. As the plunger of the syringe is withdrawn, a negative pressure is created at the inlet port 112. The primary check valve 140 prevents fluid flow from the outlet port 116 to the inlet port 112. Upon a sufficient negative pressure at the inlet port 112, the pressure gradient necessary to actuate the secondary check valve 150 (i.e., the cracking pressure) will be realized and fluid will flow through the secondary check valve 150 to the inlet port 112. When a sufficient quantity of fluid has passed through the secondary check valve 150, the negative pressure may be terminated by stopping the withdrawal of the plunger.

A positive pressure may then be produced at the inlet port 112 by depressing the plunger. A sufficient positive pressure at the inlet port 112, or a sufficient negative pressure at the outlet port 116 will exceed the cracking pressure of the primary check valve 140 and the fluid will flow through the primary check valve 140 to the outlet port 116. The secondary check valve 150 prevents the positive pressure at the inlet port 112 from causing fluid to flow from the inlet port 112 to the secondary inlet port 114.

The cracking pressure of the primary and secondary check valves 140, 150 may be chosen so as to permit a very small negative pressure to cause fluid to pass through the secondary check valve 150 to the inlet portion 112. Alternatively, the seat member 70 and valve member 50 may be disposed to provide that the secondary check valve 150 may be assembled within the dual check valve 110 to provide a high cracking pressure, thereby requiring a substantial negative pressure at the inlet port 112 to actuate the secondary valve 150. Further, while the secondary check valve 150 may have a high cracking pressure, requiring a substantial negative pressure at the inlet 112 in order to actuate the secondary check valve 150, the primary check valve 140 may have a low cracking pressure which is actuated by a slight positive pressure at the inlet port 112. Any combination of cracking pressures for the primary and secondary check valves 140, 150 may be employed through the appropriate assembly of the primary and secondary check valves 140, 150.

Although the present invention has been described in terms of particular embodiments, it is not limited to these embodiments. Alternative embodiments and modifications which would still be encompassed by the invention can be made by those skilled in the art, particularly in light of the foregoing teachings. Alternative embodiments, modifications, or equivalents may be included within the spirit and scope of the invention as defined by the claims.

What is claimed is:

1. A check valve for regulating fluid flow, said check valve having a forward flow direction in which flow through said valve occurs at a predetermined cracking pressure and a reverse flow direction in which flow through said valve is prevented, said check valve comprising:
   a housing comprising a channel having an inlet section and an outlet section, said inlet and outlet sections comprising respective luer fittings for connection to medical devices;
   a seat member including a seating portion, said seat member including a passageway;
   a valve member, said valve member including a body portion and an elastomeric valve flange portion forming a valve cavity which receives said seating portion to form a sealing interface therebetween over a seal length L, said valve flange portion (i) being sealed to said body portion to prevent fluid flow therebetween, and (ii) being axially positioned with respect to said seating portion to provide a force which urges said valve flange portion against said seating portion to yield a predetermined cracking pressure for said check valve, said force being comprised of an axial component and a radial component, said members being configured such that said radial component is substantially greater than said axial component, said elastomeric valve flange portion expanding in response to positive fluid pressures greater than said cracking pressure at said inlet section to form an area between said valve flange portion and said seating portion for passage of fluid therebetween, said members configured to at least maintain said seal length L in response to substantial reverse pressure to prevent fluid flow in said reverse flow direction, said body portion being retained by a portion of said housing to prevent axial movement of said valve member away from said seat member in said forward flow direction.

2. A check valve as defined in claim 1, wherein said channel includes a central axis extending between said inlet section and said outlet section, and said seat member is coaxially aligned with said central axis, said passageway being coaxially disposed in said seat member.

3. A check valve as defined in claim 1, wherein said seating portion has a conical configuration such that said interface of said seating portion with said elastomeric valve flange portion forms a seal length therebetween.

4. A check valve as defined in claim 1, wherein said elastomeric valve flange portion forms a frusto-conical valve cavity such that contact with said seating portion forms a seal length therebetween.

5. A check valve as defined in claim 1, wherein said inlet section has a diameter of approximately 0.15 inches.

6. A check valve as defined in claim 1, wherein said elastomeric valve flange portion expands in response to positive fluid pressure at said inlet section to form an annular area between said valve flange portion and said seating portion for passage of fluid therebetween, said valve flange portion sufficiently elastic to expand by an amount which yields an annular area approximately equal to or greater than the area of said passageway in said seat member without exceeding the elastic limit of said valve flange portion.

7. A check valve as defined in claim 6, wherein said housing surrounds said valve-flange portion and wherein said valve flange portion is sufficiently elastic to permit said valve flange portion to expand to a dimension equal to the interior dimension of said channel.

8. A check valve for regulating fluid flow, said check valve having a forward flow direction in which flow through said valve occurs at a predetermined cracking pressure and a reverse flow direction in which flow through said valve is prevented, said check valve comprising:
   a housing comprising a channel having an inlet section and an outlet section, said housing additionally comprising a transition section between said inlet section and said outlet section, said transition section being coaxially aligned with said inlet section and said outlet section, said transition section including a plurality of axially oriented ribs extending radially inward from a periphery of said transition section;

a seat member including a seating portion, said seat member including a passageway;

a valve member, said valve member including a body portion and an elastomeric valve flange portion forming a valve cavity which receives said seating portion to form a sealing interface therebetween, said valve flange portion (i) being sealed to said body portion to prevent fluid flow therebetween, and (ii) being axially positioned with respect to said seating portion to provide a force which urges said valve flange portion against said seating portion to yield a predetermined cracking pressure for said check valve, said force being comprised of an axial component and a radial component, said members being configured such that said radial component is substantially greater than said axial component, said body portion abutting and being retained by a portion of said housing to prevent axial movement of said valve member away from said seat member.

9. A check valve as defined in claim 8, wherein said ribs are separated by an angular distance so as to create a plurality of lumens through which fluid may pass.

10. A check valve for regulating fluid flow, said check valve having a forward flow direction in which flow through said valve occurs at a predetermined cracking pressure and a reverse flow direction in which flow through said valve is prevented, said check valve comprising:

a housing comprising a channel having an inlet section and an outlet section;

a seat member including a seating portion, said seat member including a passageway;

a valve member, said valve member including a body portion and an elastomeric valve flange portion forming a valve cavity which receives said seating portion to form a sealing interface therebetween, said valve flange portion (i) being sealed to said body portion to prevent fluid flow therebetween, and (ii) being axially positioned with respect to said seating portion to provide a force which urges said valve flange portion against said seating portion to yield a predetermined cracking pressure for said check valve, said force being comprised of an axial component and a radial component, said members being configured such that said radial component is substantially greater than said axial component, said elastomeric valve flange portion expanding in response to positive fluid pressure at said inlet section to form an annular area between said valve flange portion and said seating portion for passage of fluid therebetween, said valve flange portion sufficiently elastic to expand to contact an interior wall of said channel without exceeding the elastic limit of said valve flange portion, said check valve including at least one relief passage on either or both of said channel walls or said valve flange portion to permit fluid flow through said valve when said valve flange portion expands to contact said wall of said channel, said body portion abutting and being retained by a portion of said housing to prevent axial movement of said valve member away from said seat member.

11. A check valve for regulating fluid flow, said check valve having a forward flow direction in which flow through said valve occurs at a predetermined cracking pressure and a reverse flow direction in which flow through said valve is prevented, said check valve comprising:

a housing comprising a channel having an inlet section and an outlet section;

a seat member including a seating portion and a retaining portion sized to create an interference fit with a wall of said inlet section, said seating portion being integrally affixed to said retaining portion, said seat member including a passageway;

a valve member, said valve member including a body portion and an elastomeric valve flange portion forming a valve cavity which receives said seating portion to form a sealing interface therebetween, said valve flange portion (i) being sealed to said body portion to prevent fluid flow therebetween, and (ii) being axially positioned with respect to said seating portion to provide a force which urges said valve flange portion against said seating portion to yield a predetermined cracking pressure for said check valve, said force being comprised of an axial component and a radial component, said members being configured such that said radial component is substantially greater than said axial component, said body portion abutting and being retained by a portion of said housing to prevent axial movement of said valve member away from said seat member.

12. A check valve for regulating fluid flow, said check valve having a forward flow direction in which flow through said valve occurs at a predetermined cracking pressure and a reverse flow direction in which flow through said valve is prevented, said check valve comprising:

a housing comprising a channel having an inlet section and an outlet section;

a seat member including a seating portion, said seat member including a passageway;

a valve member, said valve member including a body portion and an elastomeric valve flange portion forming a valve cavity which receives said seating portion to form a sealing interface therebetween, said valve flange portion (i) being sealed to said body portion to prevent fluid flow therebetween, and (ii) being axially positioned with respect to said seating portion to provide a force which urges said valve flange portion against said seating portion to yield a predetermined cracking pressure for said check valve, said force being comprised of an axial component and a radial component, said members being configured such that said radial component is substantially greater than said axial component, said valve member including an orientation portion affixed to said body portion, and a shoulder between said orientation portion and said body portion for abutting a portion of said housing to retain said body portion and prevent axial movement of said valve member away from said seat member, said orientation portion having a smaller diameter than said body portion.

13. A check valve, comprising:

a housing comprising a channel for conducting fluid, said channel having a longitudinal axis, said housing including luer fittings for connection of medical devices thereto;

a first check valve member disposed in said channel along said longitudinal axis; and a second check valve member disposed in said channel along said longitudinal axis, one of said members having a valve portion comprised of an elastomeric material for applying a sealing force to the other of said members along a sealing interface having a seal length L, at least one of said members having a sealing surface which is inclined relative to said longitudinal axis such that said sealing force varies in response to the relative axial position of said members in said channel, said channel configured to permit one of said members to be axially positioned with respect to the other of said members at multiple positions corresponding to multiple cracking pressures, said members relatively axially positioned at one of said multiple positions to provide a predetermined cracking pressure for said check valve, said elastomeric material being responsive to fluid pressure greater than said cracking pressure in a forward flow direction to provide an opening between said members for fluid flow in said forward fluid flow direction, said members configured to at least maintain said seal length L in response to substantial fluid pressure in a reverse flow direction to prevent said fluid flow in said reverse fluid flow direction.

14. A check valve as defined in claim 13, wherein said check valve members are configured such that said elastomeric material forcibly biases said members axially in opposite directions.

15. A check valve as defined in claim 13, wherein one of said valve members includes a conical portion and the other said valve member includes a valve cavity sized to receive said conical portion.

16. A check valve, as defined in claim 13, wherein one of said valve members further comprises a passageway through said member, said passageway providing fluid communication through said member.

17. A check valve as defined in claim 13, wherein said check valve members are configured such that said sealing force comprises an axial component and a radial component, said radial component being greater than said axial component.

18. A check valve as defined in claim 13, wherein one of said valve members is affixed to a wall of said channel, so that axial displacement of said member relative to said wall is prevented.

19. A check valve as defined in claim 18, wherein one of said valve members is sized to provide an interference fit with said wall.

20. A check valve, as defined in claim 13, wherein one of said members is movable in a direction of reverse flow such that said substantial fluid pressure in said reverse flow direction drives said valve portion axially to increase said seal length L.

21. A check valve, as defined in claim 13, wherein said seal length is sufficiently long to seal around particulate matter trapped in said sealing interface.

22. A check valve comprising:
a housing comprising a channel for conducting fluid, said channel having a longitudinal axis;
a first check valve member disposed in said channel along said longitudinal axis; and
a second check valve member disposed in said channel along said longitudinal axis, one of said members having a valve portion comprised of an elastomeric material for applying a sealing force to the other of said members said elastomeric material being responsive to fluid pressure such that said fluid pressure drives said elastomeric material toward a wall of said channel to release said sealing force, either or both of said elastomeric material or said channel wall having a relief passage to prevent complete stoppage of fluid flow due to said driving of said elastomeric material, at least one of said members having a sealing surface which is inclined relative to said longitudinal axis such that said sealing force varies in response to the relative axial position of said members in said channel, said channel configured to permit one of said members to be axially positioned with respect to the other of said members at multiple positions corresponding to multiple cracking pressures, said members relatively axially positioned at one of said multiple positions to provide a predetermined cracking pressure for said check valve.

23. A method of manufacturing a check valve, comprising:
inserting a first check valve member through a female luer opening into a channel of a female luer fitting;
inserting a second check valve member into said channel of said female luer fitting; and
adjusting the cracking pressure of said check valve by relatively axially positioning said members in said channel of said female luer fitting.

24. A method as defined by claim 23, wherein said steps of inserting comprises sliding said members through a portion of said channel which has a substantially uniform cross-section.

25. A dual check valve, comprising:
first and second check valves in fluid communication, each of said check valves comprising:
a housing comprising a channel for conducting fluid, said channel having a longitudinal axis;
a first check valve member disposed in said channel along said longitudinal axis; and
a second check valve member disposed in said channel along said longitudinal axis, one of said members having a valve portion comprised of an elastomeric material for applying a sealing force to the other of said members along a sealing interface having a sealing length at least one of said members having a sealing surface which is inclined relative to said longitudinal axis such that said sealing force varies in response to the relative axial position of said members in said channel, said channel configured to permit one of said members to be axially positioned with respect to the other of said members at multiple positions corresponding to multiple cracking pressures, said members relatively axially positioned at one of said multiple positions to provide a predetermined cracking pressure for said check valve, said elastomeric material being responsive to fluid pressure greater than said cracking pressure in a forward flow direction to provide an opening between said members for fluid flow in said forward fluid flow direction, said members configured to at least maintain said seal length in response to substantial fluid pressure in a reverse flow direction to prevent said fluid flow in said reverse flow direction; and
said first and second check valves being responsive to negative pressure at an inlet to said first check valve such that said second check valve opens in response to said negative pressure while said first check valve remains closed, said first and second check valves being responsive to positive pressure at said inlet to said first check valve such that said first check valve opens while said second check valves remains closed.

26. The dual check valve of claim 25, wherein the predetermined cracking pressure for said first check valve is greater than the predetermined cracking pressure for the second check valve.

* * * * *